United States Patent [19]
VandenBerg

[11] Patent Number: 5,850,005
[45] Date of Patent: Dec. 15, 1998

[54] CUT FLOWERS AND PROPAGATING MATERIAL OF THE CRYSANTHEMUM PLANT NAMED YELLOW VERO

[75] Inventor: Cornelis P. VandenBerg, Salinas, Calif.

[73] Assignee: Yoder Brothers, Inc., Alva, Fla.

[21] Appl. No.: 229,114

[22] Filed: Aug. 5, 1988

Related U.S. Application Data

[62] Division of Ser. No. 173,722, Mar. 25, 1988, Pat. No. Plant 6,943.

[51] Int. Cl.$^6$ ............................... A01H 5/00; A01H 1/00
[52] U.S. Cl. .................................. 800/200; 800/DIG. 12; 47/58; 47/DIG. 1; Plt./78; Plt./74.1
[58] Field of Search ............................. Plt./74, 78, 74.1; 800/1, 200, DIG. 12; 47/58, DIG. 1

[56] References Cited

U.S. PATENT DOCUMENTS

| | | | |
|---|---|---|---|
| P.P. 6,399 | 11/1988 | Duffett et al. | Plt./74 |
| P.P. 6,943 | 7/1989 | VandenBerg | Plt./74 |
| P.P. 6,954 | 7/1989 | VandenBerg | Plt./82.2 |

OTHER PUBLICATIONS

"Mutation Breeding of Chrysanthemums", C. Broertjes, Association Euratom–ITAL, Wageningen, Euphytica 15 (1966): 156–162.

"Chrysanthemum and Rose Mutations Induced by X Rays", A.P. Chan, Plant Research Institute, Canada Dept. of Agriculture, Ottawa, Canada; reprinted from Proceedings of the American Society for Horticultural Science, vol. 88, 1966 (pp. 613–620).

"Application of Mutation Breeding Methods in the Improvement of Vegetatively Propagated Crops", C. Broertjes, Institute for Atomic Sciences in Agriculture, Association Euratom–ITAL, Wageningen, The Netherlands 1978 (pp. 162–175).

"A mutant of a Mutant . . . Irradiation of Progressive Radiation–Induced Mutants in a Mutation–Breeding Programme with *Chrysanthemum Morifolium* Ram.", C. Broertjes, P. Koene and J.W.H. Van Veen; Euphytica 29 (1980): 525–530.

Whealy, "Cultivar Selection can minimize chrysanthemum heat delay", *Growers Talk*.

Searle et al (1968) *Chrysanthemum the Year Pound* London, Blanfad Press, pp. 27–29.

*Primary Examiner*—Gary Benzion
*Attorney, Agent, or Firm*—Foley & Lardner

[57] ABSTRACT

A Chrysanthemum plant named Yellow Vero particularly characterized by its flat capitulum form; daisy capitulum type; yellow ray floret color; diameter across face of capitulum of up to 85 mm at maturity; uniform nine week photoperiodic flowering response to short days; medium plant height when grown as a single stem spray cut mum; and excellent tolerance to low temperatures for bud initiation and flower development.

2 Claims, 1 Drawing Sheet
(1 of 1 Drawing Sheet Filed in Color)

CUT FLOWERS AND PROPAGATING MATERIAL OF THE CRYSANTHEMUM PLANT NAMED YELLOW VERO

This is a division of application Ser. No. 173,722, filed Mar. 25, 1988 U.S. Plant Pat. No. 6,943.

The sent invention comprises a new and distinct cultivar of chrysanthemum, botanically known as *Dendranthema grandiflora*, and referred to by the cultivar name Yellow Vero.

Yellow Vero, identified as 81064A02, is a product of a mutation induction program which had the objective of creating new Chrysanthemum cultivars that would expand the color range of an existing cultivar while retaining all other traits.

Yellow Vero was discovered and selected by Cornelis P. VandenBerg on Dec. 18, 1985 in a controlled environment in Salinas, Calif. as one flowering plant within a flowering block established as rooted cuttings from stock plants which had been exposed as unrooted cuttings to an x-ray source of 1750 rads. The irradiated parent was the cultivar identified as Vero, disclosed in U.S. Plant Pat. No. 6,943.

The first act of asexual reproduction of Yellow Vero was accomplished when propagating material in the form of vegetative cuttings were taken from the initial selection in March 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Yellow Vero are firmly fixed and are retained through successive generations of asexual reproduction.

Yellow Vero has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Yellow Vero, which, in combination, distinguish this cut flower Chrysanthemum as a new and distinct cultivar:

1. Flat capitulum form.
2. Daisy capitulum type.
3. Yellow ray floret color.
4. Diameter across face of capitulum up to 85 mm at maturity.
5. Uniform nine week photoperiodic flowering response to short days.
6. Peduncle length ranging from 15 to 20 cm on open terminal sprays.
7. Medium plant height requiring two long day weeks prior to short days to attain a flowered plant height of 100 to 110 cm for year-round flowerings.
8. Excellent tolerance to low temperatures for bud initiation and flower development.

The accompanying photographic drawings show typical inflorescence and leaf characteristics of Yellow Vero.

BRIEF DESCRIPTION OF THE APPLICATION DRAWINGS

The file of this patent contains at least one drawing executed in color. A copy of this patent with a color drawing will be provided by the Patent and Trademark Office upon request and payment of the necessary fee.

The accompanying photographic drawing shows typical inflorescence and leaf characteristics of Yellow Vero, with the colors being as nearly true as possible with illustrations of this type.

FIG. 1 comprises a color photograph illustrating in perspective view a plant of Yellow Vero grown as a single stem cut spray mum.

Of the commercial cultivars known to the inventor, the most similar in comparison to Yellow Vero is the parent cultivar Vero. All traits of Yellow Vero are similar to those of Vero, except the color of ray florets. The color of the ray florets of Yellow Vero is a bright yellow, whereas Vero has white ray florets.

In the following description, color references are made to The Royal Horticultural Society Color Chart. The color values were determined on plant material grown as a single stem cut spray mum in Salinas, Calif. on Oct. 17, 1987.

Classification:
 Botanical.—*Dendranthema grandiflora*, cv Yellow Vero.
 Commercial.—Daisy cut spray mum.

Inflorescence

A. Capitulum:
 Form.—Flat.
 Type.—Daisy.
 Diameter across face.—Up to 85 mm at maturity.
B. Corolla of ray florets:
 Color (general tonality from a distance of three meters).—Yellow.
 Color (upper surface).—5B, oxidizing to 5C. The photographic color is less intense.
 Color (under surface).—4C.
 Shape.—Flat, oblong.
C. Corolla of disc florets:
 Color (mature).—Closest to 12A to 12B.
 Color (immature).—Closest to 144A to 144B.
D. Reproductive organs:
 Androecium.—Present on disc florets only; scant pollen.
 Gynoecium.—Present on both ray and disc florets.

Plant

A. General appearance:
 Height.—Medium; 100 to 110 cm as a single stem cut mum with two long day weeks prior to short days.
B. Foliage:
 Color (upper surface).—137A.
 Color (under surface).—137B.
 Shape.—Lobed and slightly serrated.

I claim:

1. Cut flowers of the chrysanthemum plant named Yellow Vero having the combined characteristics of flat capitulum form, daisy capitulum type, capitulum diameter of approximately 85 mm when the flower is fully open, ray floret color of RHS 5B when the flower is open and fresh, oxidizing to 5C, mature disc floret color of approximately RHS 12A to 12B, uniform nine week photoperiodic flower response to short days, excellent tolerance to low temperatures for bud initiation and flower development, and lobed and serrated leaves the upper surfaces of which are RHS 137A in color.

2. Propagating material of the Chrysanthemum plant named Yellow Vero which has the combined characteristics of flat capitulum form, daisy capitulum type, capitulum diameter of up to 85 mm when the flower is fully open, ray floret color of RHS 5B when the flower is open and fresh, oxidizing to 5C, for upper surface of flower, mature disc floret color of approximately RHS 12A to 12B, uniform nine week photoperiodic flower response to short days, excellent tolerance to low temperatures for bud initiation and flower development, and lobed and serrated leaves the upper surfaces of which are RHS 137A in color.

* * * * *